4,138,999

United States Patent [19]
Eckhart et al.

[11] 4,138,999
[45] Feb. 13, 1979

[54] ANATOMY TESTING AND MEASURING DEVICE

[75] Inventors: Thomas D. Eckhart, R.R. 2, Nevada, Iowa 50201; Richard L. Nelson, Oelwein; Jack M. Hoglan, Independence, both of Iowa

[73] Assignee: Thomas D. Eckhart, Nevada, Iowa

[21] Appl. No.: 736,692

[22] Filed: Oct. 29, 1976
(Under 37 CFR 1.47)

[51] Int. Cl.² ............................................. A61B 10/00
[52] U.S. Cl. ...................................... 128/2 V; 73/597; 73/599
[58] Field of Search ................ 128/2 V, 24 A; 73/597-600, 604, 67.5 R, 67.7, 67.8 R, 69

[56] References Cited
U.S. PATENT DOCUMENTS

| | | | |
|---|---|---|---|
| 3,238,767 | 3/1966 | Clynes | 128/24 A |
| 3,345,863 | 10/1967 | Henry et al. | 73/597 |
| 3,681,977 | 8/1972 | Wendt et al. | 128/2 V |
| 4,016,750 | 4/1977 | Green | 128/2 V |
| 4,016,862 | 3/1977 | Lancee et al. | 128/2 V |

FOREIGN PATENT DOCUMENTS 1287967  3/1962  Fed. Rep. of Germany ....... 73/67.5 R

OTHER PUBLICATIONS

"An Ultrasound Moving Target Indicator System for Diagnostic Use", Barnes, R. W. et al., IEEE Trans. on Biomed. Engr., BME-18 #1, Jan. 1971, pp. 1-8.

*Primary Examiner*—Robert W. Michell
*Assistant Examiner*—Francis J. Jaworski
*Attorney, Agent, or Firm*—Zarley, McKee, Thomte, Voorhees & Sease

[57] ABSTRACT

A circuit means including a power source, a cathode ray tube, a source of high frequency sound, a transducer means for emitting and receiving sound signals, and mode control means for varying the visible output of energy across said cathode ray tube for making various anatomical measurements by emitting high frequency sound into an anatomy through said transducer, whereby the amplitude and frequency of reflected signals received by said transducer will be visibly reflected on said cathode ray tube.

7 Claims, 6 Drawing Figures

ANATOMY TESTING AND MEASURING DEVICE

BACKGROUND OF INVENTION

The practice of selection for certain production characteristics in livestock dates from prehistoric time. Traits are considered important because of the economic values which contribute to the usefulness of animals as a source of meat protein.

Animals processing superior inheritance must be recognized by the breeder in order to make genetic improvement. Until recent times, selection in swine has been based largely upon visual appraisal. It is more effective, however, to take precise measurements of economically important traits so that selection can be employed to achieve progress in these areas.

Among those traits considered important are reproductive efficiency and body composition. Early efforts involved the measurement of fat and meat content of the live animal by use of mechanical devices and ultrasound. Selection for reduction of backfat thickness in the live animal constitutes an important genetic factor for improvement of the lean-to-fat ratio. It is possible to make animal breeding progress by use of such information on animals in the animal breeding scheme.

Other efforts have been employed to determine factors relating to reproductive efficiency. Such efforts include biopsy of vaginal genitalia as well as Doppler methods. In the case of Doppler methods, a degree of difficulty rested with operator technique in the required ability to differentiate between "noise" levels of the environment and those related to fetal blood flow. Biopsy techniques were laborious and required additional laboratory facilities and were not practical to utilize on a large sale. Use of ultrasound with a transmitting and receiving unit, however, makes it possible to identify the presence of certain characteristics rather than their movement.

SUMMARY OF THE INVENTION

Pregnancy is determined by the increase in fluid content of the uterus. The amount of amnion fluid increases rapidly from 30 to 80 days after conception. The amount of fluid gradually declines after 80 to 90 days of gestation.

A narrow beam of high frequency sound (ultrasound) is sent into the sow or cow. Echoes which bounce back from inside the animal are carefully analyzed by the device to detect the presence of fluid and fetus in the uterus. The electronic circuits have been developed to be particularly sensitive to echoes received from a uterus containing amniotic fluid and fetus. Accuracy is greatest from 30 to 65 days after conception. Results obtained outside these limits are generally less accurate.

Measurement of backfat thickness of replacement animals for the breeding program is also possible with an ultrasound device. The layers between the backfat permit ultrasound measurement of backfat depth. Actual scale readout directly on the screen allows collection of performance information for improved herd quality through selection of superior individuals.

Heretofore, efforts had been employed to measure backfat thickness and to detect sow pregnancy utilizing separate devices. Commercial animal production makes it necessary that the animal caretaker be concerned about both measurement needs. To incorporate these needs into a single device makes the invention more practical and useful.

Calibration requirements of this development make the versatility possible. That is, it is possible to search for certain intra-abdominal characteristics from the exterior of an animal in the case of sow pregnancy diagnosis. Likewise, it is possible to use the same device and transducer to search for backfat thickness along the dorsal midline area of an amimal. Both areas of use, however, require unique calibration. In the case of pregnancy diagnosis, it is necessary to use a scale reduction for observation of information on the cathode ray tube. The anatomical dimension and reference of certain characteristics makes this necessary to use an economically durable and feasible unit. In the case of backfat measurement, it is appropriate to use a readout scale on a one-to-one ratio because of the quantitative nature of backfat. General cases of measurement include measurements of one and one-half inches or less total backfat thickness. In the case of sow pregnancy diagnosis, a scale reduction of four-to-one and greater is sometimes required.

Measurement of backfat thickness that is quick and convenient is possible by use of the device in the proper setting. Furthermore, it is necessary to utilize other technology of monitoring the display so that it is accurate and so that the practice can be carried out in a convenient and efficient manner.

Differences exist in the anatomical dimension and reference of certain characteristics among species in the case of pregnancy diagnosis that also warrant special calibration. That is, the total dimension between the ventral abdominal wall and the position of the uterus with amnionic fluid will differ between swine and cattle. It is also understood that differences will occur in respect to the stage of pregnancy.

It is therefore an object of this invention to provide an anatomy testing and measuring device which through selection of different modes in the control circuit, the unit can be tested, pregnancy of animals of varying sizes, i.e., cattle or swine, can be determined, or animal backfat can be measured.

DESCRIPTION OF DRAWINGS

This invention consists in the construction, arrangements and combination of the various parts of the device, whereby the objects contemplated are attained as hereinafter more fully set forth, specifically pointed out in the claims, and illustrated in the accompanying drawings in which:

Figure 1:
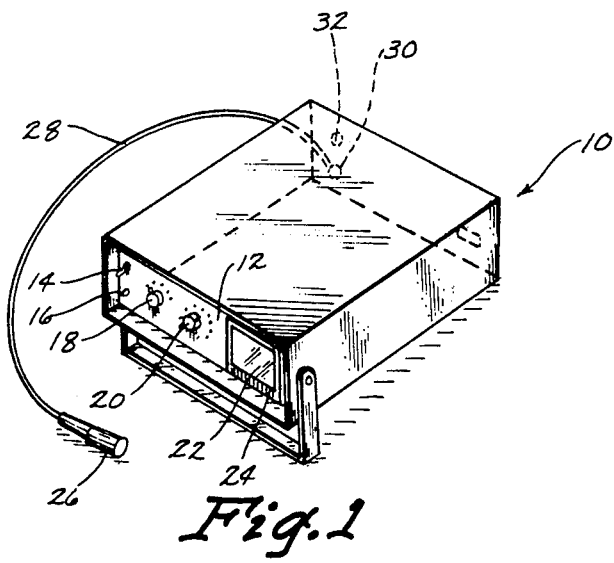
FIG. 1 is a perspective view of the device of this invention.

The housing 10 has a forward control panel 12, tone selector switch 14, power indicator light 16, mode control switch 18, gain control switch 20, cathode ray tube screen 22, and scale 24. The transducer 26 is connected by lead 28 to connector 30. Connector 30 and the test connector 32 are mounted on the rear of housing 10.

Figure 6:
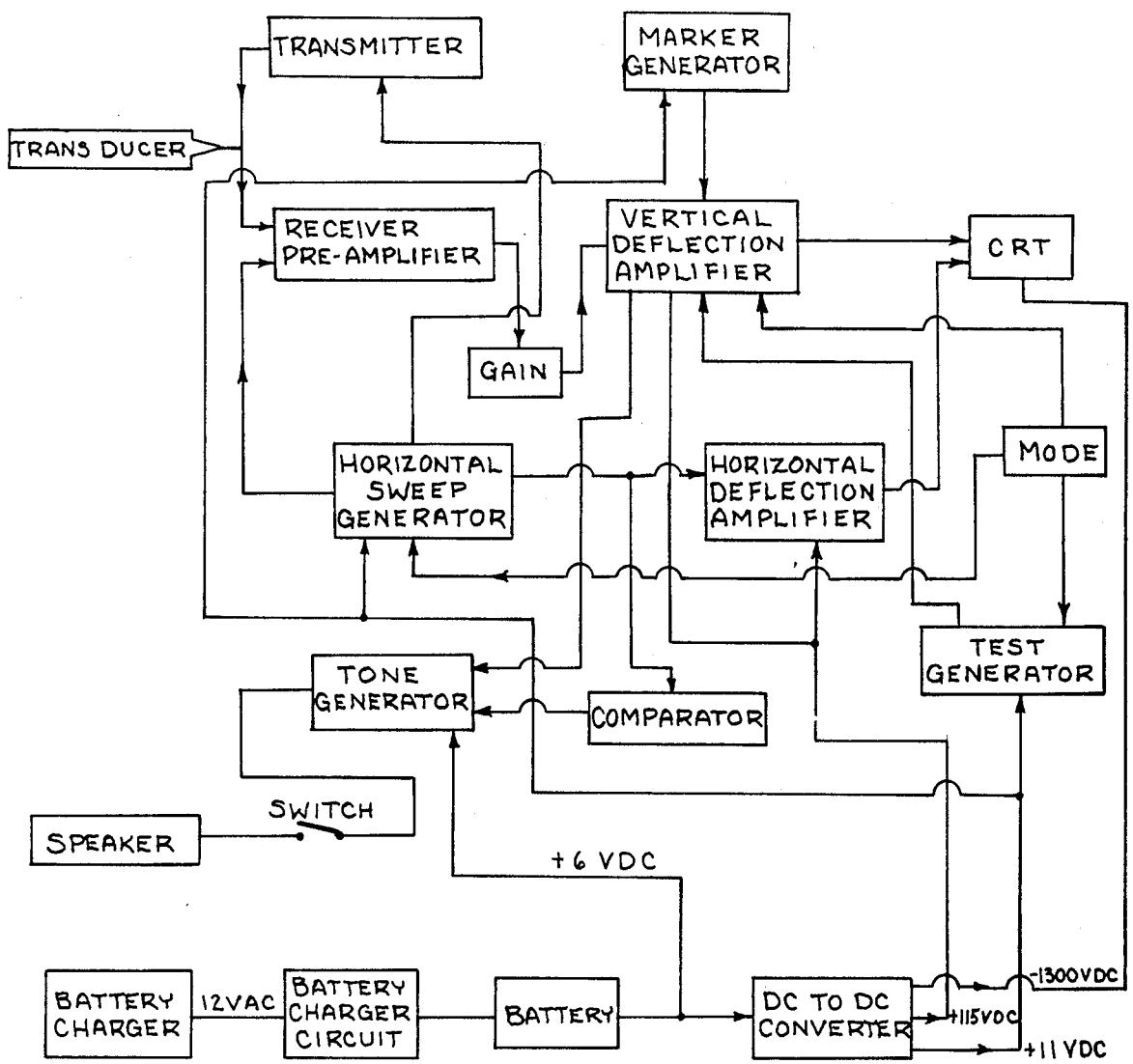
FIG. 6 is a schematic view of the circuitry of the device of this invention.

With reference to FIG. 6, the master circuitry is depicted with the various components thereof being noted thereon.

PREFERRED OPERATION

Pregnancy is determined by the increase in fluid content of the uterus. The amount of amnion fluid increases rapidly from 30 to 80 days after conception. The amount of fluid gradually declines after 80 to 90 days of gestation.

A narrow beam of high frequency sound (ultrasound) is sent into the animal. Echoes which bounce back from inside the sow are carefully analyzed to detect the presence of fluid and fetus in the uterus. The circuit of FIG. 6 has been developed to be particularly sensitive to echoes received from a uterus containing amniotic fluid and fetus. Accuracy is greatest from 30 to 65 days after conception. Results obtained outside these limits are generally less accurate.

The transducer is also capable of receiving as well as transmitting ultrasound energy. An echo or return signal will result with the transmitted energy encounters a change in tissue type of density. The time interval between transmitting the pulse and receiving the echo is directly proportional to the distance the signal travels. Ultrasound energy travels through living animal tissue at a rate of 6.3 microseconds per centimeter. Therefore, for an echo reflected at a tissue depth of one centimeter and traveling back to the transducer transducer, the calibration of the instrument is based on 12.6 microseconds per centimeter.

The reflected energy is received by the transducer, which converts it to an electrical signal. This signal is amplified and applied to the vertical push-pull deflection amplifier causing the trace to move in the Y axis. A gain control on the front panel adjusts the amount of vertical deflection. For a given gain setting, the stronger the reflected signal, the greater the vertical deflection.

The ultrasound energy is attenuated by an amount proportional to the distance it travels. To compensate for this the gain of the preamplifier is automatically increased for reflected signals that arrive from greater distances (at a later time). The transmitted pulse is also amplified by the receiver preamp and appears as a vertical pulse at the extreme left side of the CRT. An adjustment is provided to set the height of this pulse to a convenient level.

Reflected signals will appear on the CRT to the right of the transmitted pulse—the farther they appear to the right the greater the distance they were reflected from. The amount of vertical deflection indicates the relative strength of the reflected signal.

In modes other than "backfat", a marker generator provides three equally spaced triad markers along the horizontal base line of the CRT trace.

A test generator is provided to simulate a "positive" pregnancy indication. The output of this generator appears on the rear panel connector 32, and is present only in the test mode. To observe this signal properly, connect the coaxial cable 28 to connector 32. By varying the "gain" control the height of the test signal can be varied.

An audible signal is provided for convenience. The tone sounds if the tone switch is on and a signal on the right hand half of the trace exceeds approximately ⅓ the height of the CRT.

This device also measures backfat thickness of replacement gilts. The layers between the backfat permit ultrasound measurement of backfat depth. Actual scale readout directly on the scale 24 allows collection of performance information for improved herd quality through selection of superior individuals.

USE OF THE MODE CONTROL

The switch 14 is turned to an off position whenever the instrument is not in use or when the battery is being recharged.

The switch 18 is in the test position to check the accuracy of the electronic system. The transducer probe 26 is detached from the cable 28 and plugged into the receptacle 32 in the upper right hand corner of the back panel. The other end is plugged into the receptacle 30. A vertical peak forms in the middle of the third triad of the visual screen with gain setting at 3 or more. The audible tone sounds when this peak is ⅓ or more in height of the total screen.

To test sows for pregnancy, the switch 18 is turned to the S. Preg. position. Note that three triads appear on the screen FIG. 4.

Figure 3:
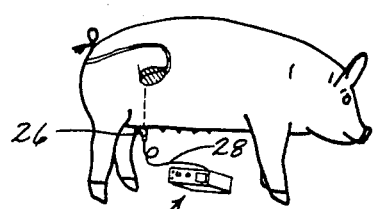
FIG. 3 is a view of a sow being tested for pregnancy.
Figure 2:
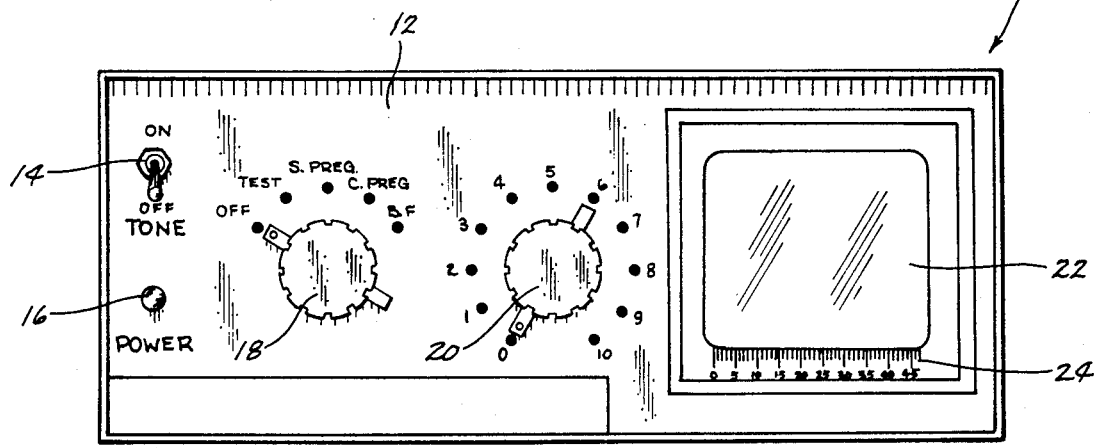
FIG. 2 is a front elevation thereof.

The gain control is turned to a position of 4 to 6. Oil is placed on the end of the probe 26, which is placed against the sow's body at a point half way between teat line and the side just below the flanks approximately 2 inches (50 millimeters) in front of the ham (See FIG. 3).

The beam of ultrasound is aimed up into the body of the sow as though aiming it at the back bone. By rotating the probe very gently back and forth, the ultrasound beam scans across the animal to obtain echoes from the uterus.

The presence of amniotic fluid and fetus in the uterus is shown by a vertical peak on the visual screen in the third triad and by the audible sound of the tone.

Figure 4:
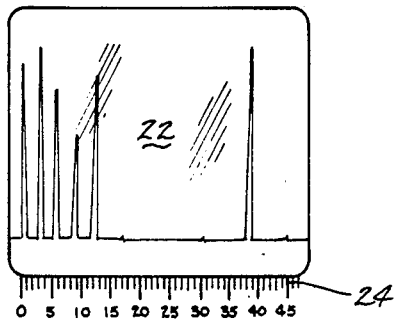
FIG. 4 is a typical screen readout for a pregnant sow.

A pregnant sow will reflect the reading on screen 22 as shown in FIG. 4. A non-pregnant sow will not reveal the right hand vertical peak signal in FIG. 4.

To check pregnancy in cattle, the switch 18 is turned to the C. Preg. position. This serves to permit a reflected signal of greater length to be procured occasioned by the larger size of the animal. In the C. Preg. position, the display screen calibration is increased by 33% and divided into quadrants rather than triads, with each quadrant being equal to one triad. After 30 to 90 days after conception, the transducer is applied to the hollow on the anterior edge of the cow's hooks, and the screen 22 is read in the manner described above. Between 4 and 5 months of pregnancy, the transducer is applied to the right hand side of the cow in substantially the same way that it was applied to the sows, as described above. On cattle, a special focus transducer is desirable to minimize the dilution of the ultrasonic signals.

Hogs to be tested should weigh between 200 and 280 pounds (91 and 127 kilograms). Collect data by weighing animals at the time of testing and adjust the data to 240 pounds (119 kilograms).

Typical operating instructions are as follows. Turn the mode control to the B.F. position and set the gain control to a position between 4 and 6 for instrument operation. The tone switch should be turned off.

Animals may be tested in a natural standing position. Usually, better cooperation can be obtained if animals are slightly hungry and fed as needed to maintain this position.

Apply heavy oil to the end of the probe or on the animal's back to insure airless contact with the hog's body. Place the probe against the hog's back at longitudinally spaced points on the sow's back.

Place the end of the probe on the animal's back area approximately 1.5 inches (40 millimeters) from the midline and hold the probe perpendicular to the surface of the skin. Readout of the backfat layers is possible on the screen and graduation scale directly in millimeters.

Figure 5:
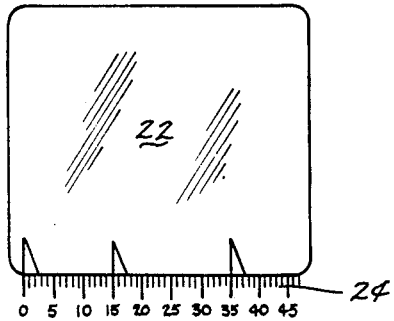
FIG. 5 is a typical screen readout for a hog backfat measurement.

Thin tissue layers within the backfat appear as vertical peak signals on the visual screen. For total measurement of backfat thickness, expect two major vertical peaks and possibly a third peak very close to the second peak. On fatter animals, be sure to include the third peak in the total measurement (See FIG. 5).

Thus, from the foregoing, it is seen that this invention achieves its stated objectives.

What is claimed is:

1. An anatomy testing and measuring device for determining pregnancy and measuring backfat, copmprising,
   a housing having an outer surface,
   a first circuit means within said housing for electrically generating ultrasonic pulses, transmitting said pulses into an animal body, receiving the echoes of said pulses from said animal body, selectively processing said pulses for visual display, and visually displaying said pulses to determine pregnancy in a sow, pregnancy in a cow and to measure the backfat of cattle,
   said first circuit means having electrically interconnected transmitter means, receiver means, and a cathode ray tube display means with a multiposition mode switch means,
   said cathode ray tube display means having a cathode ray tube on said outer surface, a horizontal sweep generator, a horizontal deflection amplifier, a vertical deflection amplifier, a gain control means, and said mode switch means electrically interconnected,
   said mode switch means having at least first, second and third positions, said first position selecting a first predetermined sweep rate of said sweep generator and a first predetermined level of the base line of the display on said cathode ray tube to determine pregnancy in a sow, said second position selecting a second predetermined sweep rate of said sweep generator and a second predetermined level of said base line of the display on said cathode ray tube to determine pregnancy in a cow and said third position selecting a third predetermined sweep rate of said sweep generator and a third predetermined level of said base line of the display on said cathode ray tube to determine backfat thickness,
   a transducer means remote from said housing and electrically connected to said first circuit means for transmitting ultrasonic pulses into said animal body and receiving the echoes of said pulses, and
   power means for powering said first circuit means.

2. The device of claim 1 wherein a second circuit means for comparing the amplitude of a transmitted pulse to the amplitude of the corresponding echo pulse is electrically connected to said first circuit means, said second circuit means having an audible generating means such that an audible tone is generated when said amplitude of said echo pulse is a predetermined height relative to said amplitude of said transmitted pulse.

3. The device of claim 1 wherein a third circuit means for testing said first circuit means and said transducer means is electrically connected to said first circuit means, said third circuit means having a test generator adapted to electrically simulate a pregnant condition and connection means for detachably connecting said transducer means to said test generator such that connection of said transducer means to said connecting means and activation of said test generator produces a positive pregnancy test on said cathode ray tube.

4. The device of claim 3 where said mode switch means comprises a fourth position, said fourth position adapted to activate said test generator.

5. The device of claim 1 wherein a marker generator is electrically connected to said first circuit means so that three equally spaced triad markers are provided on said base line of said display for said first and second positions of said mode switch means.

6. The device of claim 1 wherein said third predetermined level of said base line is positioned below said display so that said display does not show said base line.

7. The device of claim 6 wherein a scale is imposed along the bottom portion of said display of said cathode ray tube, said scale adapted to provide direct readout of backfat thickness.

* * * * *